(12) United States Patent
Lovschall et al.

(10) Patent No.: US 8,722,100 B2
(45) Date of Patent: May 13, 2014

(54) MINERAL TRIOXIDE AGGREGATE (MTA) COMPOSITION AND USE

(75) Inventors: Henrik Lovschall, Silkeborg (DK); Pia Kjaergaard, Grena (DK); Jesper Skovhus Thomsen, Aarhus C (DK)

(73) Assignee: Dentosolve, Silkeborg (DK)

( * ) Notice: Subject to any disclaimer, the term of this patent is extended or adjusted under 35 U.S.C. 154(b) by 283 days.

(21) Appl. No.: 13/393,515

(22) PCT Filed: Aug. 27, 2010

(86) PCT No.: PCT/DK2010/050222
§ 371 (c)(1),
(2), (4) Date: Feb. 29, 2012

(87) PCT Pub. No.: WO2011/023199
PCT Pub. Date: Mar. 3, 2011

(65) Prior Publication Data
US 2012/0156308 A1    Jun. 21, 2012

(51) Int. Cl.
*A61K 6/06*     (2006.01)
*A61P 1/02*     (2006.01)
*A61K 33/24*    (2006.01)
*A61K 33/16*    (2006.01)

(52) U.S. Cl.
USPC .......................................... 424/602; 106/35

(58) Field of Classification Search
USPC ........................................................ 106/35
See application file for complete search history.

(56) References Cited

U.S. PATENT DOCUMENTS

| | | | |
|---|---|---|---|
| 4,569,954 A | 2/1986 | Wilson | |
| 5,415,547 A | 5/1995 | Torabinejad et al. | |
| 5,769,638 A | 6/1998 | Torabinejad et al. | |
| 6,264,472 B1 | 7/2001 | Okada et al. | |
| 6,756,421 B1 | 6/2004 | Todo et al. | |
| 8,075,680 B2 * | 12/2011 | Mongiorgi et al. | 106/35 |
| 2003/0087986 A1 | 5/2003 | Mitra | |
| 2003/0113686 A1 | 6/2003 | Jia | |
| 2004/0226478 A1 | 11/2004 | Primus | |
| 2005/0263036 A1 | 12/2005 | Primus | |
| 2007/0009858 A1 | 1/2007 | Hatton et al. | |

FOREIGN PATENT DOCUMENTS

| | | |
|---|---|---|
| EP | 0 329 268 A2 | 8/1989 |
| RU | 2 197 940 C1 | 2/2003 |
| WO | WO-9208438 | 5/1992 |
| WO | WO-2004/108095 A1 | 12/2004 |
| WO | WO-2008/100451 A2 | 8/2008 |
| WO | WO-2008/103712 A2 | 8/2008 |
| WO | WO-2009/025599 A1 | 2/2009 |

OTHER PUBLICATIONS

Annette Wiegand et al., Review on floride-releasing restorative materials-floride release and uptake characteristics, antibacterial activity and influence on caries formation, *Dental Materials—Science Direct*, 2007, pp. 343-362, vol. 23, Elsevier.
Chia-Tze Kao et al., Properties of an Accelerated Mineral Trioxide Aggregate-like.Root-end Filling Material, *JOE*, Feb. 2009, pp. 239-242, vol. 35, No. 2.
Rafael Grajower et al., Observations on a Calcium hydroxide lining in retrieved deciduous teeth, with proximal amalgam fillings, *Journal of Oral Rehabilitation*, 1984, pp. 561-569, vol. 11.
H. Schweikl et al., Genetic and Cellular Toxicology of Dental Resin Monomers, *J. Dent Res*, 2006, pp. 870-877, vol. 85, SAGE.
Michel Goldberg et al., Cells and Extracellular Matrices of Dentin and Pulp: A Biological Basis for Repair and Tissue Engineering, *CROBM*, 2004, pp. 13-27, vol. 15, SAGE.
J. Camilleri et al., The Chemical constitution and biocompatibility of accelerated Portland cement for endodontic use, *International Endodontic Journal*, 2005, pp. 834-842, vol. 38.
Phillip L. Tomson et al., Dissolution of bio-active dentine matrix components by mineral trioxide aggregate, *Journal of Dentistry—Science Direct*, 2007, pp. 636-642, vol. 35, Elsevier.
Mikako Hayashi et al., Ways of enhancing pulp preservation by stepwise excavation—A systematic review, *Journal of Dentistry—Science Direct*, 2011, pp. 95-107, vol. 39, Elsevier.
Maria Giovanna et al., Biomimetic remineralization of human dentin using promising innovative calcium-silicate hybrid "smart" materials, *Dental Materials—Science Direct*, 2011, pp. 1055-1069, vol. 27, Elsevier.
Jessie F. Reyes-Carmona et al., Biomineralization Ability and Interaction of Mineral Trioxide Aggregate and White Portland Cement with Dentin in a Phosphate-containing Fluid, *JOE*, May 2009, pp. 731-736, vol. 35.

* cited by examiner

*Primary Examiner* — Walter Webb
(74) *Attorney, Agent, or Firm* — Muncy, Geissler, Olds & Lowe, P.C.

(57) ABSTRACT

The present application discloses a fast-setting mineral trioxide aggregate (MTA) with fluoride release for practical treatment of diseases in teeth and bone, e.g. for caries treatment and/or prevention. The cariostatic MTA contain calcia-silica-alumina cement with moderately increased tricalcium aluminate content allowing high calcium hydroxide release. The MTA composition support remineralization and biomineralization, and it is suitable for stimulation of hard tissue regeneration. MTA embodiments contain superplasticizer and nanosilicate for improved mechanical properties. The MTA compositions include optional radiocontrast and nano-enriched leachable fluorine, nitrate, strontium, and phosphate. The fast-setting MTA paste exhibits flow-to-clay-like consistency, which allows new practical applications including cavity lining, temporary restoration, bonding, and cementations in one MTA embodiment. The high calcium hydroxide and high fluoride release are suitable for caries prevention and treatment, and per se inhibition of dental symptoms.

18 Claims, 1 Drawing Sheet

MINERAL TRIOXIDE AGGREGATE (MTA) COMPOSITION AND USE

FIELD OF THE INVENTION

The present invention relates to mineral trioxide aggregate (MTA) comprising a powdered material and an aqueous hydration liquid, as well as a kit comprising the system, that primarily consists of fast-setting calcia, silica, alumina system and additives including fluorine and polyacid-based hydration enhancing material for prevention and treatment of disease in teeth and bone, including treatment and prevention of dental caries.

BACKGROUND OF THE INVENTION

The tooth is covered with enamel containing hydroxyapatite which is insoluble in the oral environment. Saliva contain abundant minerals close to saturation at normal pH. Fluoride ions in water, from tooth paste, et cetera, can exchange hydroxyl groups in apatite in the teeth. Fluorapatite has lower solubility and it is more acid resistant than hydroxyapatite.

Caries is a disease wherein acid produced by bacteria induce damage by dissolving enamel, dentin, cementum, and potentially bone. These tissues progressively become soft and may eventually break down as 'holes'. The use of fluorines in fast-setting MTA for caries prevention and treatment has not been described previously.

The minerals in teeth and surrounding fluids are in a back-and-forth exchange. When a neutral pH at the surface of the tooth drops below 5.5, demineralization proceeds faster than remineralization and the mineral structure on the tooth surface can decay and be damaged. Several tooth pastes and also dental materials release fluoride for caries prevention. However, some dental materials are also acidic, which in part may promote demineralization and growth of bacteria.

Glass-ionomer cements with fluoride release have been considered as long-term provisional restorations, however, actually it is not proven by prospective clinical studies whether secondary caries has been significantly reduced by fluoride release from restorative low pH glass ionomer materials (Wiegand et al. 2007). The use of fluorines in fast-setting materials with high pH, such as alkaline MTA for caries prevention has not been described previously.

The 'nerve' or the dental pulp is soft tissue with nerves in the center of a tooth. The pulp is surrounded by dental hard tissues. The pulp chamber extends from the crown and down through the root canals. If dental caries or dental traumas are left untreated 'the nerve' in the crown and root canals may get infected by bacteria. Such lesions may progrediate and spread through root canals and surrounding bone. Endodontic treatments of pulp and root canals can cure infections or traumas and save the tooth.

Vital pulp tissue can be capped with wound paste if the exposure is clean and small. However, at signs of infection it is often necessary to remove the pulp tissue and clean the pulp chamber and root canals. When this is done, the root canals are sealed and the overlying cavity is filled. Combined prevention and practical treatment of caries and pulp disease by using one fast-setting MTA composition has not been described previously.

The MTA invention introduced by Torabinejad et al. contains Portland cement powder and radiopacitizer particles (US 2005/0263036A1, U.S. Pat. No. 5,415,547). It has primarily been used as an endodontic sealing material in and around teeth. Interestingly, MTA sets in a humid environment, and furthermore it has a high alkalinity which counteracts oral bacteria (U.S. Pat. No. 5,415,547 continued in U.S. Pat. No. 5,769,638). The setting reaction is initiated after mixing powder with water. However, the setting time of MTA is about 3 hours and the material is at risk of being displaced.

The Portland cement powder primarily consist of tricalcium silicate ($3CaO.SiO_2$; C3S), dicalcium silicate ($2CaO.SiO_2$; C2S), tricalcium aluminate ($3CaO.Al_2O_3$; C3A) and tetra calcium aluminoferrite ($(CaO)_4.Al_2O_3.Fe_2O_3$; C4AF). Calcium suphate addition in Portland cement ensures a slow turnover of calcium aluminates. Typically addition of 3-7% of calcium sulphate (gypsum, calcium sulphate dihydrate and/or anhydrite) to portland cement clinker is used for inhibition of calcium aluminate hydration. Test on clinker material for Aalborg White® (C3A<5%) portland cement production ground without gypsum demonstrated long setting times (>1 h). However, this is too long for practical dentistry, such as filling of tooth cavities. It has been unclear which types of cement clinkers ground with or without gypsum that can be used as main component in mineral trioxide aggregate with rapid and controlled setting times typically in the range of 2½-10 minutes.

Addition of calcium chloride to MTA containing Portland cement has been found to accelerate the setting time to 57±3 min (US 2007/0009858 A1). Use of cement-like material with setting times down to 14 minutes was described by (Kao et al. 2009). However, this setting time is relatively long regarding temporary fillings where fast-setting and early strength development is desirable. Typical addition of radiopacitizer to cement or MTA-like material is likely to increase the setting time. Setting times above 10 minutes are, however, impractical regarding e.g. restoration of cavities.

The use of calcium hydroxide is a key treatment modality in operative dentistry and it is used for a wide range of dental applications including caries treatments and endodontics. The use of calcium hydroxide with high solubility as liner, such as in Dycal, at the bottom of deep cavities can, however, lead to wash out of material and loss of overlying filling material (Graiower et al. 1984).

Calcium hydroxide is released from MTA by hydration of calcium oxide ($CaO+H2O \rightarrow Ca^{2+}+2OH^-$), which has favourable bacteriostatic and cariostatic effects The released calcium and hydroxyl ions provide a long-term high pH which is the basis for the important antibacterial effect of using MTA in endodontic treatments. Enterococci resist a relatively high pH of antimicrobial agents. The bacteriocidal effect of calcium hydroxide releasing agents, also on Enterococci, increase with the pH above pH 11. E. faecalis is be about 100-fold more sensitive to killing at pH 12 in comparison to pH 11. Accordingly, the MTA release of calcium hydroxide at high pH is very important.

Addition of calcium aluminates in very high amounts up to 40-60% to Portland cement produce setting times down to 15 minutes (US 2005/0263036 A1) or lower. Extensive replacement of Portland cement, or MTA, with calcium aluminate may decrease the setting time. However, addition of monstrous amount of aluminates at the expense of calcium oxide is a disadvantage. Use of high aluminate containing cement, sulfoaluminate cement, calcium fluoro-aluminate cement, or as reported 40-60% calcium aluminates in MTA (US 2005/0263036 A1) at the expense of calcium oxide, is a major disadvantage especially regarding the favorable effects of calcium hydroxide release on bacteria and caries. Under certain circumstances aluminum in high amount is considered cytotoxic. Apparently, there is a need for MTA for bacteriostatic and cariostatic treatments with fast-setting and significantly lower and moderate calcium aluminate content facilitated by limited gypsum content.

The pulpo-dentinal complex responds to external injuries with dentin sclerosis, dead tracts, and or reparative dentin. Glass ionomer cements (GIC) with fluoride have been used as dental restoration material, isolation cement material below fillings, or e.g. protection of deposited calcium hydroxide before acid etching in order to counteract calcium hydroxide liner wash-out. However, the clinical success by using such materials depends not only on the physical and chemical properties of dental materials, but also on the biological properties (Schmalz and Arenholt-Bindslev 2009).

GIC's with resins typically release chemicals such as HEMA monomer (2-hydroxyethyl methacrylate). Monomers including HEMA and TEGDMA can be eluted and cause genotoxicity and cytotoxicity (Schweikl et al. 2006), and inhibit reactionary dentinogenesis (Goldberg and Smith 2004). Furthermore, HEMA was found to be the most common sensitizer among patients referred for patch testing with acrylate test series. Therefore, the possibility of using more pulp and tissue friendly isolation materials seems relevant.

A material for endodontic treatments with polymers and surfactants, including calcia, silica, and alumina in a so-called 'dentalcrete' particulate is described in (WO 2008/08100451). Water-soluble polymers, including PVP, PVA, and hydrolyzed PVA, are used to improve the consistency, similar to using more powder and less liquid, which gives a more putty consistency. Surfactants are added in order to interact with the polymers and improve the fluidity and rheological properties. In a preferred embodiment the C3A content is 5% and the calcium sulphate content is 4%. The use of fluorines, a fast-set favourable aluminate-gypsum ratio, superplasticizer, or other additives, for caries treatment was not described.

Fine particulated MTA with a surface area of up to 1000 $m^2/kg$ has been suggested to be able to penetrate thin root canals (US 2005/0263036 A1). However, powder with very large surface area is difficult to hydrate and the powder absorbs increased amounts of water. Ultrafine ground MTA powder requires therefore a significant increase in water-powder ratio to get a manageable consistency. The use of plasticizer in order to decrease the water content was not described.

A material containing a prototype cement blending (Aalborg White®) without gypsum was reported briefly in a study on endodontic material by Camilleri et al. 2005. A non-specific superplasticizer was used for inhibition of flash setting. Details on materials, powder-liquid ratio, setting time et cetera were not reported. Use of fluorine additives, use of material with increased calcium aluminate, use of polyacid-based superplasticizer for reducing the liquid/powder ratio, for prevention and practical treatment of caries were not described.

MTA may contain Portland cement in which low solubility calcium fluoride is added in clinker material before calcination (melting) and grinding of clinkers (US 2005/0263036 A1). Pending US 2005/0263036 A1 suggest that calcium fluoride incorporated in clinker may or may not be released to the surrounding environment. Uncertainty whether calcium fluoride is released from MTA containing calcium fluoride has not been clarified.

Tooth pastes may contain components which enhance remineralization and calm symptoms in sensitive teeth. Studies described fluorine, strontium, and potassium nitrate compounds in tooth pastes may have such symptom calming effect, especially when tiny channels called dentin tubules in the tooth bone (dentin) with nerve endings are open and exposed. A disadvantage when using such materials orally is however a limited symptom calming effect on exposed tubules in a sensitive tooth below a filling.

Zink-Oxygen-Eugenol cement has been shown to decrease symptoms from sensitive teeth. However, placement of eugenol-containing hydrophobic material as intermediary filling prior to the placement of resin restorations may inhibit subsequent polymerization of monomers due to the eugenol, which also may be relatively cytotoxic. Temporary hydrophilic filling material, which both seal, bond, and restore lost dental tissue, prevent caries, decrease symptoms, and furthermore stimulate remineralization and tissue regeneration, has not been described.

OBJECT OF THE INVENTION

The purpose of the present invention is prevention and treatment of disease in teeth and bone including prevention and treatment of caries by generating a tissue friendly fast-setting MTA product which combine:
a) a high fluoride content, high pH, and symptom inhibiting components
b) increased hydration effect of liquid by using superplasticizer compound in powder or liquid, a material which is preferably biocompatible, and which improve MTA mechanical properties
c) an operational consistency, a practical fast setting time and favorable strength development.

Figure 1:
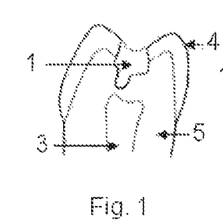
FIG. 1. Longitudinal section of tooth where caries has been removed (excavated) and the cavity, including outer part of exposed dentin, is filled and covered with fast-setting MTA (1) as semi-permanent filling.
Figure 2:
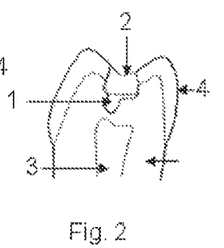
FIG. 2. Longitudinal section of tooth where caries has been removed (excavated), or has not been completely removed near the pulp, and dentin (5) and the pulp (3) is covered with fast-setting MTA (1) and the overlying cavity has a permanent filling (2).
Figure 3:
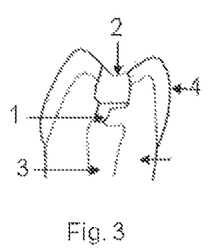
FIG. 3. Longitudinal section of tooth where caries has been removed. The vital pulp (3) exposure and the dentin (5) is capped with fast-setting MTA (1) and the cavity has a permanent filling (2).
Figure 4:
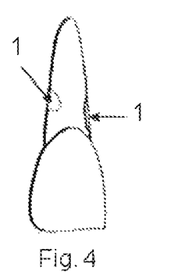
FIG. 4. Whole tooth with resorptions on the root surface, one deep and one shallow, are filled with fast-setting MTA (1).
Figure 5:
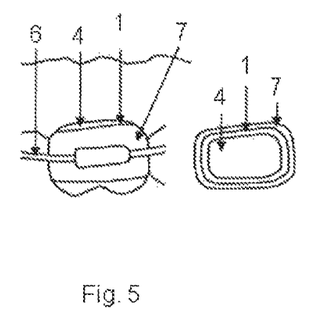
FIG. 5. Tooth fixed to a orthodontic wire (7) with a band or ring (8), which is cementated with fast-setting MTA (1) as bonding agent between the appliance (8) and the enamel (4).
Figure 6:
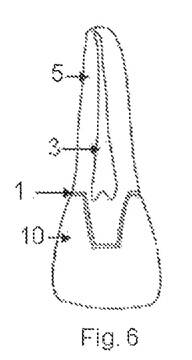
FIG. 6. Tooth (7) with a crown (prosthetic) (10) which is cementated with fast-setting MTA (1) as bonding agent between the appliance (10) and the prepared dentin (5).
Figure 7:
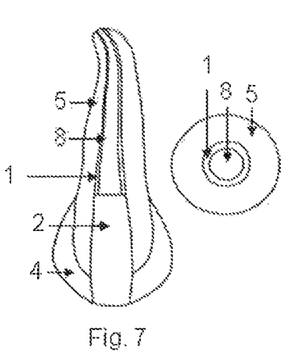
FIG. 7. Longitudinal section of root where the pulp has been removed and a narrow root canal has been prepared for obturation (root canal filling). The root is filled in direction of the root with fast-setting MTA (1) as sealer and a point (8) such as guttapercha.
Figure 8:
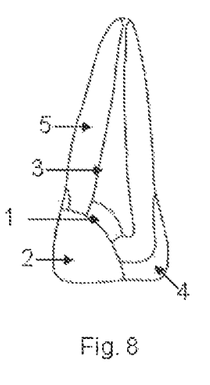
FIG. 8. Longitudinal section of tooth with trauma where dentin covering the left corner of the pulp chamber is lost. The exposed pulp (3) wound is covered with MTA (1) as pulp capping or pulpotomy agent, and covered by overlying restoration material (2).
Figure 9:
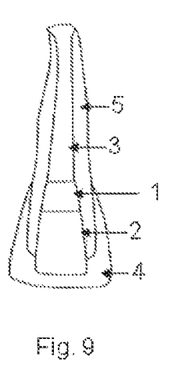
FIG. 9. Longitudinal section of tooth with trauma where dentin covering the pulp chamber and the coronal pulp have been removed. The residual pulp tissue (3) is covered with MTA (1) and overlying filling material (2) as pulpotomy with fast-setting MTA.
Figure 10:
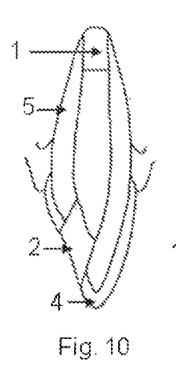
FIG. 10. Longitudinal section of tooth where the pulp has been removed and a wide root canal has been prepared for obturation through the crown (ortograde). The root-end is sealed and filled with fast-setting MTA (1) and the canal is obturated (10) and the coronal cavity filled (2).
Figure 11:
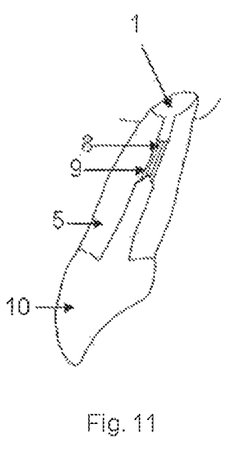
FIG. 11. Longitudinal section of tooth with a root canal filling comprising a point (8) and a sealer (9). The root-end is here prepared for root-end filling through the bone and apex (retrograde). The root-end has an apical MTA (1) filling for sealing and obturation of the canal.

In the figures, the following reference numbers are used: (1) is the fast-setting MTA according to the invention, (2) is overlying filling and restoration material, (3) is the pulp, (4) is the enamel, (5) is the dentin, (6) is an orthodontic wire, (7) is the orthodontic band on tooth, (8) is a point, (9) is the sealer, and (10) is a crown (prosthetic).

DETAILED DISCLOSURE OF THE INVENTION

The present invention relates to a fast-setting fluoride-releasing mineral trioxide aggregate (MTA) dental material, and to the use thereof in caries treatment and/or prevention. In one embodiment the dental material comprises:

a) more than 50%, a flash setting high aluminate cement powder or portland cement-like powder without gypsum addition, comprising:
  more than 60% calcium oxide (C);
  more than 15% silica (S), such that it comprise more than 50% calcium silicates including alite (tricalcium silicate or C3S) and belite (dicalcium silicate or C2S), with a C/S ratio above 2.0;
  more than 3% alumina (A), such that it comprises more than 7% calcium aluminates (CA);
  less than 10% sulphates ($SO_3$); altogether with a particle surface area of more than 200 $m^2$/kg,
b) 0.001-49.9% by dry weight of one or more fluorine-containing additive material with a particle surface area of 200 to 300,000 $m^2$/kg;
c) 1-49.9% by dry weight of one or more additives with a particle surface area of 200 to 300,000 $m^2$/kg; and
d) a hydration liquid optionally comprising more than 0.001% by weight of the liquid of one or more soluble powder additives; and
e) 0.001-10.0% by weight of the liquid of one or more super-plasticizers; and
wherein said hydration liquid, d), constitutes 10-45% by weight based on the total MTA weight of a)-e).

The invention also relates to kits for the preparation of the dental material.

CSA-Cement

A main constituent of the material is the more than 50% by dry weight of a flash setting moderate high aluminate cement powder or Portland cement-like powder without gypsum addition (referred to herein as "CSA-cement"). The CSA-cement typically constitutes such as 53-95% by dry weight, preferably such as 69-79% by dry weight.

The main powder component is typically ball mill grinded raw clinkers comprising primarily calcia, silica, and alumina, and it may include sulphates, although sulphates are not needed. By using a preferential selection of moderate high aluminate containing CSA-cement, e.g. raw material clinker ground with low sulphate below 10% or without sulphate, it is possible to produce a fast-setting MTA. When little or no gypsum has been added to a ground portland cement clinker, the hydration of C3A is rapid and the hexagonal-plate calcium aluminate hydrates start forming in large amounts soon after the addition of water, causing almost an instantaneous set. The present invention thereby solves the problem of using slow setting powdered clinker material with low aluminate content.

By purposely selection of CSA cement material comprising a moderate tricalcium aluminate content >7% C3A ground with low or without calcium sulphate or gypsum addition it is possible to avoid using calcium aluminate in large amounts as described previously at the expense of calcium oxide, which with water release calcium hydroxide. Depending on the composition of CSA cement material, a specific gypsum and sulphate content is indicated for optimum performance of the fast-setting MTA. By using a raw material clinker ground without gypsum and with low sulphate below 10%, such as 0-4%, preferably 0-2% sulphate, it is possible to produce a fast-setting MTA.

In order to obtain MTA setting times which are practical for operative dentistry essentially in the range 2½-10 minutes, this invention select as main component CSA cement with a moderate high tricalcium aluminate content C3A >7%, preferably about 10% C3A ground without gypsum. Furthermore, by using such fast-setting CSA as main powder component it is possible to mix MTA powder and liquid with substantial amount of purposely selected additives comprising fluorines with favorable effects on caries and symptoms, and at the same time get a favorable consistency and practical setting time.

The hydration of calcium oxide in MTA release calcium and hydroxyl ions which gives a high pH in humid environment which not only has an anti-bacterial effect. Furthermore, high pH contrary to low pH, enhance remineralization of teeth. A layer of crystallized hydroxyl apatite is formed on the surface of the MTA material. The combination of soluble hydroxyl ions and calcium ions, and furthermore fluor ions and phosphate ions, stimulate apatite formation, including biomineralization of hydroxylapaptite ($Ca_{10}(PO_4)_6(OH)_2$) and fluoroapatite ($Ca_5(PO_4)_3F$), especially in the calcium and phosphate ion rich fluids in the oral environment.

The use of calciumhydroxide with high solubility as liner may lead to wash out of material and subsequent displacement or loss of overlying filling material. These problems are solved as the present fast-setting MTA release calcium hydroxide at remineralization enhancing high pH with coincident high early strength development, and subsequent long-term compression stability.

The CSA-cement is further characterized by having included therein more than 60% by dry weight of calcium oxide (C), which constitutes such as 65-75% by dry weight, such as preferably 67.5%.

It also comprises more than 15% by solids weight of silica (S), which constitutes such as 22-30% by dry weight, such as preferably around 23.5%.

The calcium oxide and silica are present in such amounts that the CSA-cement comprises more than 50%, such as 60-80%, by dry weight of calcium silicates including alite (tricalcium silicate or C3S) which e.g. constitutes 40-60% by dry weight, such as 47-57%, preferably 51.7% (Bogue composition), and belite (dicalcium silicate or C2S) which e.g. constitutes 20-40% by dry weight, such as 24-34%, preferably 28.6% (Bogue composition). Preferably, the C/S weight ratio, i.e. the weight ratio between calcium oxide and silica, is above ratio 2.0, such as ratio 2.5-3.5 preferably ratio 2.9.

The CSA-cement further comprises more than 3% by dry weight of alumina (A), such as 3.2-8%, such as preferably below 5%, preferably 4.1% by dry weight of alumina (A/$Al_2O_3$). The calcium oxide and alumina are further present in such amounts that the CSA-cement comprises more than 7% by weigh of calcium aluminates (CA) or tricalcium aluminates (C3A), which e.g. constitutes 8-22% by dry weight, such as 10-15%, preferably 10.0° A) (C3A, Bogue composition).

As described the CSA-cement comprises less than 10% by dry weight of sulphates ($SO_3$). The use of raw material clinker ground without gypsum and with low sulphate below 10° A) typically 0-4%, such as preferably 0-2%, preferably with 1.48% or without sulphate, makes it possible to produce MTA with fast setting time.

In some embodiments, the cement further comprises more than 0.001% fluorines.

The CSA-cement has a particle surface area of more than 200-250 $m^2$/kg, typically in the range 400-600 $m^2$/kg, and most preferably at 490 $m^2$/kg.

In one embodiment, the main CSA-cement material include 68% of type I or type III (ASTM) white Portland cement clinker comprising (by Bogue calculation) more than 8% and less than 13% by dry weight of tricalcium aluminate (C3A) in powder, in which sulphate content is about 1.5%, the ratio of CaO to $SO_3$ is above 2.0, and the alkali content is equal to or less than 0.6%—determined as $Na_2O+0.65K_2O$, and in which tetra aluminoferrite (C4AF) is lower than 15% and content of iron oxides in total powder is lower than 0.5%—a material which is finely ground without added gypsum ($CaSO_4.2H_2O$) or added calcium sulphates to a particle surface area of 400-1000 $m^2$/kg.

Additives in General

By using purposely selected additives, in analogy to the use of components and materials in tooth pastes with cariostatic or desensitizing effects, the invention produces improved MTA for practical dental treatment, which firstly has more direct effect on tooth surfaces in contact, surrounding tissue, cavities and channels, secondly has improved cariostatic and symptom relieving effects, and thirdly accomplish a controlled fast setting time for practical use in operative dentistry.

Purposely selection of compounds, such as fluoride, potassium, nitrate, strontium, and phosphate compounds, as additive in fast-setting MTA powder and or water phase, can similarly to the use of fluoride, potassium, nitrate, strontium, and phosphate compounds in tooth pastes, improve the local exposure of local hard tissue in contact with MTA, such as exposed dentin in an excavated cavity with post-operative symptoms, and thereby essentially support prevention and treatment of disease and symptoms. As demonstrated in specific embodiments below the invention describe several examples of using leachable fluorines, nitrate- and strontium salts, and phosphates, as additives.

Fluorine-Containing Additive Material

Fluorines are purposely selected as MTA additive in order to be released and stimulate remineralization, inhibit caries, and dental symptoms, and potentially assist inhibition of bacterial metabolism. Release of soluble fluoride from MTA increase the remineralization processes in dental hard tissue in contact with the MTA material, e.g. in cavities filled with MTA. It is well known that fluoride has a caries inhibiting effect.

The working mechanism of fluoride on caries has been described as (i) an inhibitory effect on bacterial metabolism at high fluoride concentrations, (ii) an inhibition of demineralization when fluoride is present at the crystal surfaces during bacterial acid attack, and (iii) on crystal surfaces both a promoting effect on remineralization and formation of a layer of fluorapatite-like material (Feierskov et al. 1996).

Free fluoride and calcium ions in solution released from MTA react and form calcium fluoride ($CaF_2$), which has a lower solubility product. However, fluoride thereby promotes more CaO is dissolved as calcium hydroxide ions, which eventually support a high pH which is favorable for remineralization.

The material of the invention comprises 0.001-49.9%, e.g. 0.05-49.9%, 0.1-49.9%, or 0.1-20% by dry weight of one or more fluorine-containing additives, such as 1.1-15% by dry weight, and in some interesting embodiments the material comprises 2.5-5.1% by dry weight of the one or more fluorine-containing additives.

The particle surface area of the one or more fluorine-containing additives is above 200 $m^2$/kg, typically ultrafine fluorine particles are used with a surface area at 600 to 300,000 $m^2$/kg, preferably as nano- or nanoenriched micro-powder with several particles <1 µm for enhanced fluoride release. Even the normally quite insoluble calcium fluoride can thereby leach fluoride at increased rate.

The fast-setting MTA contain one or more additive fluorines, practically in an amount less than the amount of main fast-setting CSA component. Fast-setting MTA powder in some embodiments contain fluorines selected from calcium fluoride ($CaF_2$), stannous fluoride ($SnF_2$), sodium fluoride (NaF), strontium fluoride ($SrF_2$), calcium monofluorophosphate ($CaFPO_3$), sodium monofluorophosphate ($Na_2FPO_3$), sodium hexafluorosilicate ($Na_2SiF6$), ytterbium fluoride ($YbF_3$), fluoroapatite ($Ca_5(PO_4)_3F$), organic fluoride/amine fluoride (Org/AmF), and mixtures thereof, preferably with a particle surface area of 200 to 300,000 $m^2$/kg, typically of 400-2000 $m^2$/kg, and preferably above 600 $m^2$/kg. The dissolution rate of practically insoluble fluorines can be increased significantly by fine particulation in the micro- and nano-range.

Fine Particulation

The size of the solid compounds (i.e. the cement, the fluorine-containing additives and the further additives) can be reduced by milling essentially by using planetary ball mill (Retsch, PM100) with zirconium grinding jars and balls, or by using jet mill, air mill, or hydro mill, to produce nanoscale or microscale powders. Fine particulation of individual fast-setting MTA powder components, particles, compounds, additives and fractions hereof, increase the surface area. Particles with increased surface has increased rate of dissolution and thereby increased release of soluble compounds, such as hydroxyl ions (pH), fluoride, calcium, potassium, strontium, nitrate, and phosphate, to the humid oral environment.

Addition of finely particulated leachable and soluble additive, in the powder or in the water phase (hydration liquid), significantly increase the release of the dissolved material from fast-setting MTA in humid environments. By adding very fine particulated material it thereby is possible to observe not only short-term but also long-term release at a significantly higher level from the fast-setting MTA in aqueous environment.

Total ultrafine particulation of fast-setting MTA powder composition or fraction thereof provide a nano-enriched material with increased number of submicro- and nano-particles, which due to the relative high surface area release significantly more soluble material per volume and thereby increase the release rate of materials such as calcium hydroxide and fluoride.

Very fine powder which has been particulated intensively requires unfortunately large amount of water for hydration of the larger particle surface, and the water pore volume between the particles thereby get bigger. Very low particle sizes thereby make MTA more porous and thus reduce its strength. However, by using superplasticizer it is possible to decrease the liquid-powder ratio. By mixing ultrafine or nano-enriched fast-setting MTA powder with a water phase containing polyacid-based superplasticizer it is possible to hydrate the particles, form a usable paste, and minimize the amount of water phase. Vice versa, by increasing the particle size, i.e. decreasing the surface area to 250 $m^2/kg$ in MTA the need for using superplasticizer decrease.

The embodiment of this invention contain as a key feature leachable fluorines, specifically selected or made, as extraordinarily fine particulated additives, which increase short- and long-term fluoride release from fast-setting MTA in aqueous environment after setting.

Further Additives

Purposely selected additives are typically added as isolated powder fraction in MTA powder. The MTA material includes 1-49.9%, such as 1-48.9%, by dry weight of one or more purposely selected powder additives in the MTA. In some embodiments, such further additives constitutes 1-30% by dry weight, e.g. 1.5-25%, such as 15-25% by dry weight However, it is evident that such further additives also can be added as a component in 'remainder material' in CSA-cement, and e.g. be added to clinker raw material before calcination in a kiln.

The particle surface area of the further additives is 200 to 300,000 $m^2/kg$, with larger particles 200 to 600 $m^2/kg$ typically representing radiopacitizer material, fine particles 400 to 1000 $m^2/kg$, and or ultrafine particles 600 to 300,000 $m^2/kg$, representing selected leachable additives comprising very small microparticles or nanoparticles <1 μm.

By adding radiocontrast materials to fast-setting MTA it can be seen on x-ray radiographs. This is desirable in order to avoid misinterpretation of radiopacities, i.e. dark areas on dental radiographs, which could represent caries. Radiocontrast material (radiopacitizer) added in fast-setting MTA increase x-ray contrast on radiographs. X-ray contrast material typically contain atoms with atomic weight which is higher than the atom weight of calcium, in particular atoms like zirconium, strontium, bismuth, titanium, barium, tantalum, lanthanum, wolfram/tungsten, or ytterbium in atoms, molecules, compounds, powders, components, glasses, alloy, steels, cements, fillers, microparticulates, nanoparticulates, granulates or mixtures thereof.

The essential components in the main CSA powder component with fast setting is alkaline earth metal oxide, silica and alumina. The alkaline earth metal oxide in CSA cement may include calcium ions and or strontium ions within a wide range of compounds. The calcium ions in fast-setting MTA react with other compounds and can be found as diverse calcia, calcium salts, calcium aluminates, and calcium silicates. The calcium ions may be substituted with strontium ions. The additives in particular include one or more compounds selected from nitrates, silicates, nitrates, strontium, radiopacitizer compounds, and phosphates.

The phosphates can be chosen from a group, but not limited to, examples including tricalcium phosphate, calciumglycero-phosphate, calciumfluorophosphate, calcium phosphates, phosphogypsum, alpha tricalcium phosphate, beta tricalcium phosphate, dicalcium phosphate, and tetracalcium phosphate, and hydroxyapatite, preferably leachable calcium phosphates. Such additives can also be integrated into clinkers or fractions thereof during calcination.

Furthermore, the MTA can, besides the powdered component with fast-setting, essentially contain any further additive being in the physical state of crystals, glasses, granites, clay, shale, sand, slag, alloys, fillers, granulates, fibres, microfibres, nanofibres, or mixtures thereof. However, increased amount of additive at the expense of calcium oxide content typically decrease calcium hydroxide release and pH in local aqueous environment.

By purposely selecting cariostatic, bacteriostatic, desensitizing, strength enhancing, or setting time regulating components as additive it is possible to improve the MTA. The antibacterial property of fast-setting MTA can be improved, e.g. by addition of zinc oxide to powder or chlorhexidine, however, the mechanical strength of the MTA is thereby lowered markedly. Addition of releasable bioactive substances, such as addition of alkaline phosphatase enzyme, growth factors, and or differentiation factors may increase the regenerative capability of the fast-setting MTA.

Hydration Liquid and Superplasticizers

The material further comprises a hydration liquid. The hydration liquid is typically mixed with the cement, the fluorine-containing additive and the further additives immediately prior to use of the dental material. The hydration liquid constitutes 10-45% by weight based on the total weight of the dental material. In some embodiments, the hydration liquid constitutes 12-30%, such as 14-25% by weight based on the total weight of the dental material. The main constituent of the hydration liquid is water. The water is preferably treated so that the main part of ions, microorganisms and other impurities have been removed. Deionized water is preferred.

The one or more superplasticizer constitutes 0.001-10.0% by weight of the hydration liquid, such as 0.1-8.0%, e.g. 0.2-5.0%, or 0.5-4%, by weigh of the hydration liquid. In some embodiments, the one or more superplasticizers are included in the hydration liquid, however, it is also possible that superplasticizer is added as powder to the MTA powder as salt or freeze-dried components. This allows the use of fast-setting MTA powder embodiments with only water as the hydration liquid.

Furthermore, it is also possible, but not mandatory, that the hydration liquid comprise one or more soluble powder additives in an amount of more than 0.001% by weight of the liquid of. Practically, hydration liquid with admixtures, superplasticizer and further soluble salts, are added to a bottle and shaken until all the salts have dissolved, and the hydration liquid is ready for use.

Examples of such soluble powder additives in the hydration liquid are potassium nitrate and sodium fluoride.

In one embodiment, the hydration liquid comprises i) 0.001-10.0% by weight of the liquid of one or more superplasticizers; and ii) more than 0.001%, such as 0.001-10.0%, e.g. 0.1-5.0%, by weight of the liquid of one or more soluble powder additives.

Superplasticizer, added in powder or liquid, can counteract the disadvantages of using increased amount of water-phase in mixed MTA paste and can thereby improve the strength. Superplasticizers gives a closer package of micro- and nano-sized particles in MTA powder, which thereby enables a reduced water-powder ratio and a smaller water pore volume, which is favorable for mechanical properties including compression strength. The strength of fast-setting MTA is inversely related to the amount of water in the water and powder mix. Frequently, by decreasing the water-powder ratio it is possible not only to increase the mechanical MTA strength, but also indirectly to decrease the associated setting time.

The superplasticizers are well-defined and chemically different from the older plasticizer products. Plasticizers for cements have been made from lignosulfonates, and superplasticizers were later developed from sulfonated naphthalene condensate and sulfonated melamine formaldehyde. The new and more biocompatible polyacid-based superplasticizers work on dispersed powder particles by steric dispersion and steric stabilization, instead of only electrostatic repulsion, which is more powerful than only electrostatic repulsion. The new generation of polycarboxylate-based superplasticizers reduces effectively the surface forces and/or adhesion between particles in fast-setting MTA paste and enable thereby a reduction of water-powder ratio.

The preferred superplasticizer is purposely selected tissue friendly and polyacid-based preferably with a neutral pH above the critical pH 5.5 of apatite demineralization. The new generation of polyacid-based superplasticizers are not only more efficient, but also more tissue friendly in comparison to especially naphthalene- and formaldehyde-based products. The chemical structure of polycarboxylate ether, polycarboxylate, or just 'polyacid-based' superplasticizers, allows for modification that can meet specific needs. Polyacid-based superplasticizers can be polyacid-based solutions, salts, salts in solution, or powder, or mixtures thereof. Polycarboxylic acid or derivatives, polycarboxylate acid derivatives or salts thereof, polycarboxylate-based powder, polycarboxylates such as sodium polycarboxylate, including polyacid-based compounds containing additional groups comprising hydroxyl, ether, or esther groups, such as polycarboxylate ethers, di- or higher esther of polycarboxylic acid, or any orally appropriate commercial polyacid-based, polyether-carboxylate-based, or polyether-polycarboxylate-based superplasticizer, can be used in hydration liquid for tissue friendly use.

The polyacids, or polycarboxylic acids, used as superplasticizer are relatively weak organic acids. They can easily be selected with a neutral pH above the critical pH 5.5 of apatite demineralization. The purposely use of polyacids is regarded both acceptable, biocompatible, and tissue friendly, especially when used together with alkaline MTA powder for dental treatments.

Strong polyacids and polycarboxylic acids have been widely used as acid in dental materials for decades. Dental resin-based materials for restoration often contain polyacid, such as polyacrylic and polymethacrylic frequently mixed with the low-viscous monomers like HEMA. Polyacids with low pH below <5.5 are used in glass-ionomer (GIC) cements for dissolution of glass material. GIC are e.g. made of fluoroaluminosilicat glass powder, polyacid and water, and mixed with setting at low pH (WO 1992/008438, WO 2004/108095, U.S. Pat. No. 6,765,038, U.S. Pat. No. 6,756,421, U.S. Pat. No. 6,264,472). Fluoride releasing glass ionomer cements (GIC) mixed with polyacid have increasingly been used for cavity lining and tooth protection. Although it frequently is thought that polyacid mixed with fluoride containing GIC powder can resist caries formation in adjacent tooth structures, clinical evidence do not fully support this (Wiegand et al. 2007).

It should be noted that the amounts of the CSA-cement, the one or more fluorine-containing additives, the one or more further additives, the one or more superplasticizers, and the (optional) one or more soluble powder additives add up to 100% by dry weight.

Preferred Embodiment

In one preferred embodiment, the dental material comprises:
a) more than 50%, a flash setting high aluminate cement powder or portland cement-like powder without gypsum addition, comprising:
   more than 60% calcium oxide (C);
   more than 15% silica (S), such that it comprise more than 50% calcium silicates including alite (tricalcium silicate or C3S) and belite (dicalcium silicate or C2S), with a C/S ratio above 2.0;
   more than 3% alumina (A), such that it comprises more than 7% calcium aluminates (CA);
   less than 10% sulphates ($SO_3$);
   altogether with a particle surface area of more than 200 $m^2/kg$,
b) 1.1-15% by dry weight of one or more fluorine-containing additive material with a particle surface area of 200 to 300,000 $m^2/kg$;
c) 1-30% by dry weight of one or more additives with a particle surface area of 200 to 300,000 $m^2/kg$; and
d) a hydration liquid optionally comprising more than 0.001% by weight of the liquid of one or more soluble powder additives; and
e) 0.2-5.0% by weight of the liquid of one or more superplasticizers; and
wherein said hydration liquid, d), constitutes 12-30% by weight based on the total MTA weight of a)-e).

In another embodiment, the dental material comprises:
a) more than 50%, such as 53-95% by dry weight, or such as preferably 69-79% by dry weight of a moderate high aluminate and flash setting cement powder or Portland cement-like powder without gypsum addition, comprising:
   a. more than 60%, such as 65-75% preferably 67.5% by dry weight of calcium oxide (C), and
   b. more than 15%, such as 22-30%, preferably 23.5% by solids weight of silica (S), such that it comprises more than 50%, such as 60-80% by dry weight of calcium silicates including alite (tricalcium silicate or C3S) and belite (dicalcium silicate or C2S), with a C/S weight ratio above 2.0. such as ratio 2.5-3.5, preferably ratio 2.9 (C is CaO), and
   c. more than 3%, such as 3.2-8%, such as preferably below 5%, preferably 4.1% by dry weight of alumina (A/$Al_2O_3$)), such that it comprises more than 7%, and constitutes 8-22%, such as 10-15%, such as preferably 10.0% by dry weight of tricalcium aluminates (C3A, Bogue composition), and
   d. an amount of 0-10%, such as 0-4% by, such preferably 0-2%, preferably 1.48% by dry weight of sulphates ($SO_3$), and
   e. altogether with a particle surface area of more than 200 $m^2/kg$, such as 250-300,000 $m^2/kg$.
b) including at least 0.1%, such as 1.1-15%, typically 2.5-5.1%, and less than 49.9% by dry weight of one or more leachable fluorine-containing additive materials with a particle surface area of 200 to 300,000 $m^2/kg$; and
c) including at least 1% and less than 48.9%, such as preferably 2-30% by dry weight of one or more additives or remainder material with a particle surface area of 200 to 300,000 $m^2/kg$; and
d) a hydration enhancing material in an amount of 0.001-10.0% by weight of hydration liquid of one or more superplasticizers typically 1-5% and preferably 2% polyacid-based superplasticizer by weight of the liquid; and
wherein said hydration liquid constitutes 10-45%, such as preferably 16-35%, by weight based on total dental material.

Fine Particulation and Superplasticizers

The MTA powder in the present invention contains discrete and individual particle fractions of suitable size i.e. fine, ultrafine, and nano-particulated powder fractions. Careful and intensive mixing of powder and hydration liquid with superplasticizer produce dense, and homogenous packing of particles. The smallest particles, especially purposely selected nano-particles such as nano-silicate, can thereby arrange in gaps between larger particles. By mixing large micro-particles and small nanoparticles together in nano-hybride MTA the gaps between relatively large particles can be filled with small particles.

By mixing powder with moderate to fine particulation e.g. 250-600 m²/kg, with limited and appropriate amount of ultrafine, nanoenriched or nanosized powder, e.g. reactive nano-silica, analogous to the material 'Densit®', it is possible to increase the MTA strength. This requires basically both the use of superplasticizer and intensive mixing of liquid and powder by using plate and hand-spatula or mix-capsules and an automated shaking machine.

Powder and Liquid Handling

Careful mixing of powders, water, solutes, additives, support packing of small nano-particles between larger micro particles, which contribute to reduction of the water pore volume. The strength and mechanical properties of fast-setting MTA is thereby improved.

Measure up and weigh the materials, pipette the hydration solution, and mix the materials together by using e.g. a suitable hand-spatula and a glass plate, thoroughly for about one minute or longer, also even if small amount of hydration liquid with superplasticizer is used, to ensure all the powder particles are hydrated.

Different designs of pre-dosed mixing capsule systems exist and anyone of these may be used. Essentially the capsule is pre-filled with powder and hydration liquid in correct amounts. The mix-capsule is first prepared and activated by bringing the powder and liquid together. The mix-capsule is then transferred to the mixing machine and mixed for a sufficient period of time, basically in the range 5-30 seconds.

The MTA material here is either mixed on a mixing pad by using a hand-spatula for 20-60 seconds, or by means of a dental capsule system for 5-30 seconds here for 20 seconds. There is essentially no significant difference on the MTA properties depending on whether the material is properly mixed by hand or by using a capsule mixing system.

Regulation of Setting Time

The setting time is controlled in a specific time range, which is practical for many dental applications i.e. 2½ to 10 minutes, by adjusting the amount of additives with accelerating or inhibiting effect on the setting reaction. The setting time can easily be fine-tuned by a professional by adjusting in very small amounts the quantity of accelerating additive such as tricalcium aluminate, or in part sodium fluoride, versus the quantity of retarding additives such as typically calcium sulphates, phosphates, or radiopacitizers.

By producing MTA with a very fast or 'a little too fast' setting it is possible to add more inhibiting additives in MTA although they have an increasing effect on the setting time. MTA embodiments with a 'little too fast' setting capability benefit from addition of additives with more or less inhibiting effect on setting, such as bismuth oxide, calcium phosphates, strontium salts, and zinc oxides.

By using purposely selected additives in specific and appropriate amounts it is possible to produce MTA for practical use with improved mechanical properties regarding caries restoration and cementation, and at the same time, achieve favorable caries preventive effects on the surrounding hard tissues.

Retarding admixtures have been suggested to form a film around reactive MTA or cement particles (e.g. by adsorption), whereby the reaction with water gets inhibited or slower. Over-dosage of retarding additives typically reduces the strength after setting. The use of additives in balanced and appropriate amounts generates controllable working and setting time in MTA suitable for treatment. The additives are purposely selected in order to accomplish the inventions purpose. The material will set initially over a period of minutes. It is simple for a professional to produce the specified fast-setting MTA embodiments and fine-tune the setting time by fine adjustment of the amount of accelerating and inhibiting additive.

Mixing of MTA Powder and Liquid

Mixing of MTA powder and hydration liquid into a paste initiates a setting reaction. The amount and reactivity of components and liquid, the surface area of particulate components, and e.g. the surface area of leachable and ultrafine fluorines, influence both the setting rate and consistency. The fast-setting MTA powder compositions specific fineness and the p/l-ratio have to be controlled in order to get appropriate working and setting time, manageable consistency, and an appropriate early strength development. By increasing the amount of ultrafine powder more hydration liquid is required, which often lead to decreased mechanical strength. The fineness of received or grinded powder components has to be controlled practically within limits, and it is favorably described as particle size range, average particle size, blaine area, maximal particle size, or the like.

MTA powder and water phase are mixed intensively with either spatula and glass plate, or most efficiently by intensive mixing in capsules on a automated mixing machine immediately prior to use. Intensive mixing minimizes the need for water phase and improves thereby consistency, stickiness, and density of set MTA.

Mixing and Consistency

The optimal MTA consistency varies according to the individual treatment and individual professional. The clinical consistency depends of the amount of powder (p) to hydration liquid (l) which operationally can be varied within limits. The powder/liquid (p/l) ratio has to be balanced carefully in order to get appropriate and useful paste consistency. The working time from start of mixing until the MTA paste no longer is workable, is relatively high typically about one minute less than the setting time. The user may cover the mixed material with a wet gauze on the mixing pad in order to inhibit evaporation.

Fast-setting MTA has unique hydrophilic properties which are favorable for sealing, however, excessive oral saliva production or dry surroundings may influence the powder-liquid ratio in the very outmost MTA surface layer. In such situations it is simple to cover the outer surface by using a water repellent strip. This will optimize the surface setting. Furthermore, this is practical for quickly filling a cavity. The water-repellent strip, film, folio, or tape should be adapted by light pressure until, e.g., a minute after, setting is experienced on the pad. Such a barrier may also be applied as a flowable layer such as e.g. varnish, resin, vaseline, oil, oily-compound, or the like.

Dynamic Working Consistency

The MTA consistency is changing during setting. The use and applicability of fast-setting MTA can thereby be expanded. Interestingly, in a specific and important according to embodiment in Example A the consistency of fast-setting MTA paste change from very flowable, to sticky, and eventually to a clay-like consistency, within few minutes. The MTA paste consistency can thereby, in a limited time frame, be used initially as a flowable lining material, and shortly thereafter as a clay-like nearly condensable material for filling a cavity, before the material sets.

Usage of Fast-Setting MTA

The combination of physical, chemical, and biological properties in one material is unique. The combination of bacteriostatic, cariostatic, sealing, biocompatible, mechanical, bonding, restorative, symptom inhibiting, regenerative, and practical properties, in one fast-setting MTA composition, are very unique and allow new dental applications. This new MTA contain only tissue-friendly materials. The material can therefore furthermore be used for protection and treatment of the pulp-dentin organ, and for stimulation of pulp-dentin regeneration.

Usage for Caries Prevention and Restoration

Mixing of MTA powder including additives with hydration liquid produce a paste with a manageable consistency which is most favorable for practical dentistry. The improved fast setting time allow a range of new practical applications.

The fast-setting MTA composition release calcium hydroxide and fluoride ions in a humid environment. In one very important embodiment according to Example A, #1-4, the material is for use in caries treatment and prevention. The fast-setting MTA maintain compression stability and even increase mechanical strength by time, despite the release of soluble components, in contrast to excessive wash-out, which has been reported e.g. after use of calcium hydroxide lining materials under overlying filling material (Grajower et al. 1984).

The new fluoride releasing MTA, with improved caristatic properties and fast setting, can be used as alternative to non-cariostatic materials as a remineralization enhancing material. MTA in contact with dentin seal and in part obturate open dentin tubules. Precipitation of minerals including apatite supports additional closure of open dentin tubules. Recent studies describe apatite biomineralization capability of MTA materials with apatite formation around and along the materials surface, such as on hard tissue surfaces with preparations, cavities, gaps, tubuli, and micro- and nano-leakages, canaliculi, especially when phosphate is present (Reyes-Carmona et al 2010) as in fast-setting MTA embodiment with fine particulated phosphate as leachable additive.

The invention also relates to a method of using the fast-setting MTA dental material as cavity liner, preventive material, and restorative material for prevention or treatment of caries and pain, for remineralization of demineralized hard tissue matrix, protection of the pulp, restoration of caries lesions, cavity lining, base filling, temporary restoration of cavities, semi-permanent filling, or inhibition of caries and step-wise excavation. The fast-setting MTA can also be used for restoration of resorption cavities and treatments of dental traumas, by the method of: 1) identifying the surface, lesion or cavity to be covered or filled; 2) preparing and cleansing the tooth surface before placement of MTA; 3) mixing fine MTA powder and hydration liquid to a paste; and 4) placement of fast-setting MTA paste. For clinical application any dispenser, applicator, syringe, pistol, gun, or the like may be used.

Usage for Cementation

The fast-setting MTA according to Example A, #5-10 can also be used where bonding or cementation of appliances including orthodontic bands, prosthetic appliances, posts, crowns, and bridges.

The invention further relates to a method of using the MTA dental material as cement for appliances, such as, posts, orthodontic bands, crowns, surgical implants, comprising the steps of: 1) identifying the site to be filled; 2) preparing the site by mechanical cleansing and irrigation for placement of MTA material; 3) mixing fine MTA powder with hydration liquid to a paste; and 4) filling or placing MTA paste on the appliance and or site for cementation.

MTA is hydrophilic materials capable of bonding to the tooth structure. The ion bonding of MTA minerals to surfaces or interfaces in relation to hard tissues or metals is of the same type as bonding of glass-ionomer cements and polycarboxylate cements (Darvell 2009). The new fast-setting MTA can also be used for bonding, luting and cementation, including cementation of orthodontic appliances, posts, crowns, bridges or the like, at relevant maximal particle sizes such as <50 µm, <25 µm, <10 µm, or <1 µm. In some embodiments within this particular use, it may not be necessary to include the further additive (item c), hence the further additive represents 0% by dry weight.

The new generation of superplasticizers markedly increase the flowability of fast-setting MTA and thereby support low film-thickness.

Use of Fast-Setting MTA with Fluoride Release for Inhibition of Symptoms

Teeth often experience increased irritability after drilling. Various physical, chemical and biological irritaments trigger symptoms or a pain response in neurons extending into exposed dentin tubules.

The fast-setting MTA can also be used for coverage and protection the tooth pulp against irritaments and associated symptoms. MTA in contact with exposed dentin support sealing of open dentin tubules. Ions released from fast-setting MTA are also basis for biomineralization and support self-sealing of open gaps and tubules. The released compounds, especially from ultrafine particulated material, enhance apatite formation and closure of gaps, dentin tubules, and micro- or nano-leakages below overlying fillings.

Furthermore, addition of leachable potassium, nitrate, and strontium salts and in fast-setting MTA, analogous to their use in toothpastes, obviously give longer and more efficient exposure of exposed dentin surfaces especially when in contact with the MTA. Specific ions released from the fast-setting MTA can thereby support alleviation of symptoms from sensitive teeth.

Specifically, small micro- and nanoparticles in MTA contribute in sealing and inhibition of bacteria and penetrate not only thin root canals (i.e. >50 µm) (US 20050263036 A1) but also dentin tubules (i.e. <3 µm), where both closing of dentinal tubules, biomineralization, and dissolution of symptom inhibiting salts support alleviation of symptoms.

Fast-setting MTA can according to embodiment in Example C and D support inhibition of potential symptoms in several ways by bonding MTA material across the dentin, sealing, precipitation of apatite, fluoride supported mineralization in tubules and gaps, and also a potential direct desensitizing potassium nitrate or e.g. strontium effect ion the pulp-dentinal neurons.

Stimulation of Tissue Regeneration

Odontoblasts a layer of cells on the inside of the dentin produce dentin around the pulp during development of the tooth, and they protect the pulp by production of extra dentin in response to irritaments. Each odontoblast has a process which extends through the dentin in a tubule.

The high pH has an alkaline hydrolytic effect on the hard tissue matrix. MTA release of calcium hydroxide is expected to support mineralization and increase the release of intrinsic growth factors from dissolved dentin matrix, and thereby stimulate pulp-dentin tissue regeneration (Tomson et al. 2007).

The fast-setting MTA has a high initial release of calcium hydroxide which can irritate soft tissue in similarly to other calcium hydroxide dental materials. Simple coverage of fast-setting MTA can protect sensitive mucosa in contact when needed.

Dental materials with resins for filling, cementation, luting and lining materials, especially with adhesive resins, may release soluble cytotoxic and genotoxic substances. The use of cytotoxic substances may lead to dentinal tubules lack odontoblasts and the pulp can thereby be more accessible to bacterial attack over time, with increased risk of long-term bacterial penetration.

By using fast-setting MTA according to Example A #1-4 as highly biocompatible, bacteriostatic, and cariostatic liner it is possible to protect the pulp-dentin organ against such soluble cytotoxic resins from overlying materials. Furthermore, it is also possible to substitute several pulp- and health-risk adhesive materials e.g. by using the fast-setting MTA material in high-strength embodiment for MTA cementation and semi-permanent restorations.

Protection of the pulp-dentin organ with biocompatible materials is important. The fast-setting MTA contain no monomers, haptens, releasable polymers, or cytotoxic degradation products, such as pro-allergic or cytotoxic adhesives and formaldehyde. The new fast-setting MTA is not only restorative, bonding, sealing, and cariostatic, but also highly tissue friendly.

Further MTA Embodiments for Prevention and Treatment of Disease

In further aspects, the invention relates to the possible use of fast-setting MTA material for prevention disease, stimulation of hard tissue regeneration, inhibition of resorptions and treatments of endodontic disease, traumas, peridontal disease, orofacial conditions, and bone defects.

The invention further relates to a method of using the MTA dental material to prevent or treat disease or symptoms, e.g. caries, endodontic disease, traumas, resorptions, peridontal disease, orthodontic conditions, orofacial dysfunction, pain, aesthetic conditions, bone defects, and pain, comprising the steps of: 1) identification of sites for MTA application in relation in relation to hard tissue surfaces and spaces; 2) preparation of hard tissue for placement of MTA such as optionally excavation, preparation, drilling, shaping, cleaning, drainage, irrigation, suction; 3) mixing of MTA powder and liquid in capsules or by using hand instrument and a plate; and introduction of MTA paste optionally by hand instrument, pistol or capsule with pipette.

In further aspects, the fast-setting MTA can be used in endodontics, where sealing, earlier setting reaction, and release of calcium hydroxide are indicated, e.g. in treatments such as sealing of root canals, orthograde or retrograde root-end filling, pulp capping, pulpotomy, wound paste, and the like.

The invention further relates to a method of using the fast-setting MTA dental material as sealer with enhanced setting reaction for filling and obturation of root canals, including bicanals, cavities, chambers, perforations, communications, and dentin tubuli, comprising the steps of (1) identifying the site to be filled, (2) preparing the root canal and associated intraradicular space by mechanical cleansing and irrigation before placement of MTA, (3) mixing MTA ultrafine powder and hydration liquid to a paste, (4) filling and sealing the root canal with a point and ultrafine MTA.

The invention still further relates to a method of using the MTA dental material as wound paste with fast setting for sealing of wound surface, pulp capping, pulpotomy, apical filling, or filling of resorptions in teeth or bone comprising the steps of: (1) identifying the wound site to be filled, (2) preparing and cleansing the soft tissue wound and surrounding hard tissue such as in root-end, root canal, pulp chamber, root surface, periodontium, pulp-dentin cavity, and related space by mechanical cleansing and irrigation for placement of filling fast-setting MTA paste therein, (3) mixing MTA powder and hydration liquid to a paste, and (4) filling or sealing the wound with MTA paste.

Embodiments in General

The present invention provides new improved fast-setting MTA with fluoride release suitable for treatment and prevention of disease as described in the following. The fast-setting MTA embodiments provide improved consistency and controlled fast-setting which facilitate practical use of MTA for a range of new treatment modalities.

The MTA embodiments here all contain superplasticizer efficiently dissolved in the hydration liquid described as weight percentage of the total hydration liquid, although superplasticizer may also be added as powder in the MTA powder composition. Supplementary additives can be integrated in clinkers during calcination as reservoir in order to supplement long-term release.

Preferred Main Powder Component

The main powder component is typically white powdered calcia, silica, and alumina material (called 'CSA-cement') with high calcium oxide content. The material has moderately increased calcium aluminate content preferable above 7% and low gypsum (calcium sulphate dihydrate) content preferably with sulphate below 2% in all MTA embodiments. On the one hand, due to the moderate tricalcium aluminate content typically at 10-12% C3A all MTA compositions have fast-setting and early strength development. On the other hand, due to moderately increased alumina content, preferably below 5% of total MTA powder weight, all specific MTA compositions allow for high calcium oxide content and thereby a wanted high calciumhydroxide release. The high presence of calcium hydroxide releasing material, rather than aluminates, thereby, fulfill the invention purpose.

The chemical composition of a typical batch is presented in the following table.

| Composition | Clinker % |
| --- | --- |
| $SiO_2$ | 23.6 |
| $Al_2O_3$ | 4.1 |
| CaO | 67.6 |
| MgO | 1.14 |
| $SO_3$ | 1.48 |
| Other | 2.08 |

The main phases present in CSA cement are abbreviated in the following way:

| Cement Chemist Notation (CCN) | Actual Formula | Name | Phase |
| --- | --- | --- | --- |
| C3S | $3\, CaO \cdot SiO_2$ | Tricalcium silicate | Alite |
| C2S | $2\, CaO \cdot SiO_2$ | Dicalcium silicate | Belite |
| C3A | $3\, CaO \cdot Al_2O_3$ | Tricalcium aluminate | Celite |
| C4AF | $4\, CaO \cdot Al_2O_3 \cdot Fe_2O_3$ | Tetracalcium alumino ferrite | Ferrite |

The Bogue composition (CCN) of main crystalline phases in a typical batch of CSA-cement is presented in the following table.

| Main phases | C3S | C2S | C3A | C4AF | Free CaO |
| --- | --- | --- | --- | --- | --- |
| Exclusive free CaO | 51 | 29 | 10 | 0.7 | 3.0 |

All the present MTA powder embodiments for prevention and treatment of caries contain fine particulated leachable fluorines in variable content.

Most examples contain radiocontrast material selected from a group comprising bismuth, zirconium, and or strontium containing materials. The fast-setting MTA embodiments frequently include radiocontrast material such as bismuth oxide, zirconium oxid, strontium fluoride, strontium oxide or hydroxide, and mixes thereof. Typically radiocontrast material represents more than 1% of fast-setting MTA material weight and frequently about 20% bismuth oxide or 20% zirconium oxide. In some applications, such as cementation of e.g. metallic orthodontic bands or posts the radiocontrast material in MTA is however not needed and can be omitted.

Additives in several examples include additives in a lesser amount such as nano silicate, fine-particulated leachable potassium nitrate, zincoxide, calcium phosphates, calcium oxide, strontium oxide, and calcium sulphate.

The powder components in each MTA composition are mixed thoroughly before use. The specific amount of each powder composition (p) has been weighed into clean mixing capsules. Sterile filtered hydration liquid (l) is added to the powder in the clean capsule according to described ratio (p/l) immediately before automated mixing for 5-20 sec, most efficiently for 20 sec, at normal room temperature.

The embodiments benefit from fine-tuning of the setting time by adjustment of the amount of inhibiting additives such as radiopacitizer, phosphates, and more efficiently calcium sulphate dihydrate/gypsum.

The clinical success rate after application of MTA and cement-like materials is critically dependent on an appropriate paste consistency. The preferred powder/liquid ratio and initial MTA consistency may vary within limits according to the specific treatment application and the individual operators preference.

All indications of percentages used herein are "by dry weight", unless otherwise specified.

EXAMPLES

The compositions of Example A-E illustrate the invention including alternative embodiments.

The amount of each powder component is described in the examples as weight percentage of the total weight of the total MTA powder composition, unless other information is described. The amount of hydration liquid is here described as microliters per gram MTA powder, and also as weight percentage of the total weight of the MTA composition. The amount of superplasticizer is descibed as weight proportion of the liquid.

Description of Raw Materials and Preparation

The final MTA composition formulation was prepared, composed, and treated according to the description below. The ultrafine particulation of additives was typically performed by using planetary ball milling (Retsch, PM100) with zirconium grinding jars and balls for 6 hours followed by fineness analysis (stereological analysis and/or Blaine measurement). The amount of materials and components in powder and hydration liquid is described in details in the Examples A-E.

The correct amounts of the materials included are weighed into an appropriate container. All powder components are weighed and liquid components pipetted with high accuracy according to the composition in the examples. The solid and powdered components are mixed intensively in a container manually or in automated powder mixer e.g. a Turbula TF, WAB. The powder and liquid described above were tested in specific embodiments as presented.

Description of Tests

The material is mixed by filling powder and liquid in the pre-determined amounts into a dental capsule system to generate the required P:L ratio and mixed for 20 seconds by using a 3M/ESPE CapMix. After mixing the MTA paste is dispensed using a suitable tool onto a plate or into any desired mould or container. Tests were performed on samples kept in a mould covered by humid gaze in a humid chamber (23±1° C.), or after storage in container and humid chamber (37±1° C.).

A sequence of tests was performed to determine influence of composition and P:L ratio on physical properties. The influence of the MTA material composition was examined in tests on setting time, radiopacity, pH, fluoride release, and compressive strength. The tests on MTA setting time and compressive strength were performed based on ISO 6876 recommendation. Gillmore apparatus with initial needle weighs (113 g, 2.12 mm dia) and final needle weighs (453.6 g, 1.06 mm dia) was used in tests on setting time; all results are mean values of at least 3 samples. Instron apparatus (Instron 5566, Instron, High Wycombe, UK) with a crosshead speed of 2 mm/min was used until fracture in tests on uniaxial compression strength; all results are mean values of at least 5 samples. The fluoride concentration was determined by electrode (Orion Research, Beverly, Mass., USA) and pH by electrode (Radiometer, Copenhagen, Denmark); at least 3 samples i.e. tablets with equal dimensions were used for each material. Each tablet sample was sealed in a flask containing deionized water.

Compression Strength of Fast-Setting MTA Embodiment with Additives Including Fluorines

| | #1 | #2 | #3 | #4 | #5 | #6 | #7 | #8 | #10 | #11 [7]Zinc-phosphate cement | #12 [8]ProRoot MTA |
|---|---|---|---|---|---|---|---|---|---|---|---|
| Cement | | | | | | | | | | | |
| [1]CSA-cement | 74.43 | 74.43 | 74.45 | 74.45 | 94.25 | 94.25 | 94.27 | 94.27 | 92.2 | | |
| F additives | | | | | | | | | | | |
| Calcium fluoride, [2]u.f. | 2 | 2.5 | 2 | 2.5 | 2 | 2.5 | 2 | 2.5 | 5 | | |
| Sodium fluoride, [2]u.f. | | | | | | | | | 0.1 | | |
| Calciumfluorophosphate, [3]fine | 0.5 | | 0.5 | | 0.5 | | 0.5 | | | | |
| Strontium fluoride, 1 μm | 1 | 1 | 1 | 1 | 1 | 1 | 1 | 1 | | | |

-continued

EXAMPLE A

|  | #1 | #2 | #3 | #4 | #5 | #6 | #7 | #8 | #10 | #11 [7]Zinc-phosphate cement | #12 [8]ProRoot MTA |
|---|---|---|---|---|---|---|---|---|---|---|---|
| Other additives |  |  |  |  |  |  |  |  |  |  |  |
| Zirconium oxide | 20 | 20 | 20 | 20 |  |  |  |  |  |  |  |
| $SiO_2$ nano | 1.7 | 1.7 | 1.7 | 1.7 | 1.7 | 1.7 | 1.7 | 1.7 | 1.7 |  |  |
| Calciumglycerophosphate | 0.02 | 0.02 |  |  | 0.02 | 0.02 |  |  |  |  |  |
| Calcium sulphate | 0.35 | 0.35 | 0.35 | 0.35 | 0.53 | 0.53 | 0.53 | 0.53 | 1 |  |  |
| Hydration Liquid |  |  |  |  |  |  |  |  |  |  |  |
| Hydration Liquid, µl per g MTA powder | 170 | 170 | 170 | 170 | 190 | 190 | 190 | 190 | 200 | 360 acid | 333 water |
| Hydration Liquid, weight in %, based on total weight of MTA | 14.5 | 14.5 | 14.5 | 14.5 | 16.0 | 16.0 | 16.0 | 16.0 | 16.7 | 26.5 | 25.0 |
| [4]Superplasticizer (PEC) | 2 | 2 | 2 | 2 | 2 | 2 | 2 | 2 | 2 |  |  |
| Tests |  |  |  |  |  |  |  |  |  |  |  |
| [5]Initial setting time (min) | 4½ | 4½ | 4½ | 4½ | 4 | 4 | 4 | 4 | 3½ | 5 | 180 |
| [6]Compression strength d1 | 95.4 | 102.0 | 101.8 | 103.5 | 101.6 | 113.8 | 118.1 | 124.9 | 107.1 | 62.3 | 77.1 |

[1]Main component: CaO 67.6%, $Al_2O_3$ 4.1%, $SiO_2$ 23.6% (C3A = 10%); 490 $m^2$/kg;
[2]ultrafine >600 $m^2$/kg;
[3]fine <600 $m^2$/kg;
[4]polyethercarboxylic acid;
[5]Gillmore test;
[6]maximal compression strength (δ-max in MPa, Instron);
[7]DeTrey;
[8]Maillefere.

Influence of Nanosilicate on Compression Strength of Fast-Setting MTA with Fluorines

| EXAMPLE B | #1 | #2 |
|---|---|---|
| Cement |  |  |
| [1]CSA-cement | 94.9 | 93.2 |
| F additives |  |  |
| Calcium fluoride, [2]u.f. | 5 | 5 |
| Sodium fluoride, [2]u.f. | 0.1 | 0.1 |
| Other additives |  |  |
| $SiO_2$ nano |  | 1.7 |
| Hydration Liquid |  |  |
| Hydration Liquid, µl per g MTA powder | 160 | 200 |
| Hydration Liquid, % of total MTA weight | 13.8 | 16.7 |
| Tests |  |  |
| [3]Superplasticizer (PC) | 2 | 2 |
| [4]Initial setting time (min) | 3½ | 3½ |
| [5]Compression strength d1 | 80.5 | 87.2 |
| [5]Compression strength d28 | 97.8 | 123.8 |

[1]Main component: CaO 67.6%, $Al_2O_3$ 4.1%, $SiO_2$ 23.6% (C3A = 10%); 490 $m^2$/kg;
[2]ultrafine >600 $m^2$/kg;
[3]polycarboxylic acid-based;
[4]Gillmore test;
[5]max. compression Strength (δ-max in MPa, Instron).

Fluoride Release from Fast-Setting MTA Embodiment with Ultrafine Particulated Fluorines

EXAMPLE C

|  | #1 | #2 | #3 | #4 | #5 | #6 | #7 | #8 [11]Dycal | #9 [11]IRM | #10 [12]Zinc-phosphate cement |
|---|---|---|---|---|---|---|---|---|---|---|
| Cement |  |  |  |  |  |  |  |  |  |  |
| [1]CSA-cement | 72 | 69 | 68 | 67 | 64 | 67 | 51 |  |  |  |
| [2]Nanoenriched fraction |  |  |  |  |  | 100% |  |  |  |  |
| Calcium aluminate, [3]u.f. |  |  |  |  |  |  | 8 |  |  |  |
| F additives |  |  |  |  |  |  |  |  |  |  |
| Calcium fluoride, [3]u.f. | 5 | 5 | 5 | 5 | 5 | 5 | 10 |  |  |  |
| Sodium fluoride, [3]u.f. | 1 | 1 |  | 1 | 1 | 1 | 1 |  |  |  |
| Strontium fluoride, 1 µm |  |  | 9 | 9 | 9 | 9 | 9 |  |  |  |

-continued

|  | EXAMPLE C | | | | | | | #8 [11]Dycal | #9 [11]IRM | #10 [12]Zinc-phosphate cement |
| --- | --- | --- | --- | --- | --- | --- | --- | --- | --- | --- |
|  | #1 | #2 | #3 | #4 | #5 | #6 | #7 | | | |
| Other additives | | | | | | | | | | |
| [4]Bismuth oxide, | 20 | 20 | 16 | 16 | 16 | 16 | 16 | | | |
| Potassium nitrate, [3]u.f. | | 5 | | | 5 | | 5 | | | |
| Calcium sulphate, [3]u.f. | 2 | | 2 | 2 | | 2 | | | | |
| Hydration Liquid | | | | | | | | | | |
| Hydration Liquid, μl per g MTA powder | 200 | 200 | 200 | 200 | 200 | 560 | 200 | | | 360 acid |
| Hydration Liquid weight in %, based on total weight of MTA | 16.7 | 16.7 | 16.7 | 16.7 | 16.7 | 35.9 | 16.7 | | | 26.5 |
| [5]Superplasticizer (PC) | 1 | 1 | 1 | 1 | 1 | 1 | | | | |
| [6]Superplasticizer (PEC) | | | | | | | 1 | | | |
| Sodium fluoride, [7]solution | + | + | + | + | + | + | + | | | |
| Potassium nitrate, [7]solution | | + | | | + | | + | | | |
| Tests | | | | | | | | | | |
| [8]Initial setting time (min) | 4 | 8 | >10 | 4 | 7 | | 3 | 3½ | | |
| [9]F in 1 L after 100 days | 0.64 | 0.62 | 1.77 | 2.41 | 2.69 | 4.09 | | 0 | | |
| [9]pH in 1 L after 100 days | 10.59 | 10.87 | 9.58 | 10.90 | 11.07 | 11.00 | | 9.9 | | |
| [10]Compression strength d1 | 46.1 | 22.8 | 66.1 | 48.6 | 20.9 | 17.7 | | 24.5 | 36.1 | 62.3 |

[1]Main component: CaO 67.6%, $Al_2O_3$ 4.1%, $SiO_2$ 23.6% (C3A = 10%; 490 $m^2$/kg);
[2]long-term ultrafine particulation of MTA powder fraction (percentage);
[3]ultrafine >600 $m^2$/kg;
[4]100% <63 μm and 60% <37 μm;
[5]polycarboxylic acid-based;
[6]polyethercarboxylic acid
[7]near-saturated;
[8]Gillmore test;
[9]tablet area = 2.21 $cm^2$;
[10]maximal compression strength (δ-max in MPa, Instron);
[11]Caulk;
[12]DeTrey.

Compression Strength of Nanoenriched Fast-Setting MTA Embodiment in Comparison to DYCAL and IRM

|  | EXAMPLE D | | | | | #6 [10]Dycal | #7 [10]IRM | #8 [11]Zinc-phosphate Cement |
| --- | --- | --- | --- | --- | --- | --- | --- | --- |
|  | #1 | #2 | #3 | #4 | #5 | | | |
| Cement | | | | | | | | |
| [1]CSA-cement | 69 | 64 | 59 | 64 | 64 | | | |
| [2]Nanoenriched fraction | | | | 50% | 100% | | | |
| F additives | | | | | | | | |
| Calcium fluoride, [3]u.f. | 5 | 5 | 5 | 5 | 5 | | | |
| Sodium fluoride, [3]u.f. | 1 | 1 | 1 | 1 | 1 | | | |
| Strontium fluoride, 1 μm | 9 | 9 | 9 | 9 | 9 | | | |
| Other additives | | | | | | | | |
| Potassium nitrate, [3]u.f. | | 5 | 10 | 5 | 5 | | | |
| [4]Bismuth oxide, | 16 | 16 | 16 | 16 | 16 | | | |
| Hydration Liquid | | | | | | | | |
| Hydration Liquid, μl per g MTA powder | 220 | 210 | 200 | 340 | 580 | | | 360 acid |
| Hydration Liquid weight in %, based on total weight of MTA | 18.0 | 17.4 | 16.7 | 25.4 | 36.7 | | | 26.5 |
| [5]Superplasticizer (PC) | 1 | 1 | 1 | 1 | 1 | | | |
| Sodium fluoride, [6]solution | + | + | + | + | + | | | |
| Potassium nitrate, [6]solution | | | + | | | | | |

-continued

| | EXAMPLE D | | | | | | | |
|---|---|---|---|---|---|---|---|---|
| | #1 | #2 | #3 | #4 | #5 | #6 [10]Dycal | #7 [10]IRM | #8 [11]Zinc-phosphate Cement |
| Tests | | | | | | | | |
| [7]Initial setting time (min) | 7 | 8 | 8 | 12 | 20 | 3½ | | |
| [9]Compression strength d1 | 41.5 | 33.3 | 12.4 | 26.2 | 10.3 | 24.5 | 36.1 | 62.3 |
| [9]Compression strength d28 | 65.0 | 63.0 | 24.7 | 45.0 | 14.0 | 33.0 | 48.3 | 102.7 |

[1]Main component: CaO 67.6%, $Al_2O_3$ 4.1%, $SiO_2$ 23.6% (C3A = 10%; 490 $m^2$/kg);
[2]long-term ultrafine particulation of MTA powder fraction (percentage);
[3]ultrafine >600 $m^2$/kg;
[4]100% <63 μm and 60% <37 μm;
[5]polycarboxylicacid-based;
[6]near-saturated;
[7]Gillmore test;
[8]tablet area = 2.21 $cm^2$;
[9]maximal compression strength (δ-max in MPa, Instron);
[10]Caulk;
[11]DeTrey.

Influence of Increased Fluorine Addition in Fast-Setting MTA Embodiment on PH

| EXAMPLE E | #1 | #2 | #3 | #4 (ref.) [9]Dycal |
|---|---|---|---|---|
| Cement | | | | |
| [1]CSA-cement | 74 | 72 | 69 | |
| F additives | | | | |
| Calcium fluoride, [2]u.f. | 5 | 5 | 5 | |
| Sodium fluoride, [2]u.f. | 1 | 3 | 6 | |
| Other additives | | | | |
| [3]Bismuth oxide | 20 | 20 | 20 | |
| Hydration Liquid | | | | |
| Hydration Liquid, μl per g MTA powder | 200 | 200 | 200 | |
| Hydration Liquid weight in %, based on total weight of MTA | 16.7 | 16.7 | 16.7 | |
| [4]Superplasticizer (PC) | 1 | 1 | 1 | |
| Sodium fluoride, [5]solution | + | + | + | |
| Tests | | | | |
| [6]Initial setting time (min) | 3½ | 7 | 8½ | |
| [7]F in 1 L after 56 days (ppm) | 0.47 | 0.85 | 1.50 | 0 |
| [8]pH in contact | 13.6 | 13.8 | 14.0 | 11.9 |
| [7]pH in 1 L after 100 days | 9.6 | 10.2 | 10.4 | 9.9 |

[1]Main component: CaO 67.6%, $Al_2O_3$ 4.1%, $SiO_2$ 23.6% (C3A = 10%; 490 $m^2$/kg);
[2]ultrafine >600 $m^2$/kg;
[3]100% <63 μm and 60% <37 μm;
[4]polycarboxylic acid-based;
[5]near-saturated;
[6]Gillmore test;
[7]tablet area = 2.21 $cm^2$, electrodes;
[8]without delay after mixing MTA paste, electrode;
[9]Caulk.

The MTA composition according to the present invention in Example A demonstrate significantly improved setting time in comparison to previous MTA. The fast-setting MTA demonstrate in cases (#1-10) improved maximal compression strength after 24 h in comparison to previous MTA (#12).

The flowable MTA paste embodiment in Example B with fluorines demonstrate that addition of nanosilicate (#2) in combination with polycarboxylic acid-based superplasticizer significantly improve the development of compression strength in fast-setting MTA without nanosilicate (#1).

The MTA embodiments in Example C were mixed at clay-like consistency. When fluorines with higher solubility are added (#1-6) the fluoride release increase further up to 2.69 ppm (#5). After extraordinary and intensive ball miling of MTA powder for 3×6 h the fluoride release increased up to 4.0 ppm (#6). Same MTA embodiment with only ultrafine calcium fluoride as fluorine additive released 0.25 ppm fluoride (however at initial setting time >10 min, not shown). The compression strength (#1-6) is compared with traditional dental cements without fluorine (#8-10).

The MTA embodiment in Example D mixed at clay-like consistency demonstrate the influence of potassium nitrate and particle size on setting time and compression strength. The strength of fast-setting MTA embodiment including 5% potassium nitrate (#2) is comparable to IRM (#7). When the same powder composition (#2, 4-5) is altered such that 50% of MTA powder (#4) is nanoenriched powder and 100% (#5) is nanoenriched powder (after 3×6 h intense ball milling) with increased surface area for increased fluoride and hydroxyl ion release rate (as in Example C) it is demonstrated that increased amount of nanoenriched fast-setting MTA powder fraction (#4) can match the compression strength of Dycal (#6).

The examination of pH according to Example E interestingly reveal that increased sodium fluoride addition in fast-setting MTA embodiment mixed at clay-like consistency both increase fluoride release and support a high pH while maintaining fast setting time. The fast-setting MTA paste with high calcium oxide content has high contact pH immediately after MTA mixing and with increased sodium fluoride content the short-term contact pH increase.

The embodiments in Example A include a range of additives with consistency and practical setting time ready for practical use. The embodiment #5-10 with nano-silicate, fluorine, and phosphate, and only minimal or practically undetectable radiocontrast material, has favorable mechanical strength e.g. for cementation of applicance, where cariostatic fluoride release is more important than radiocontrast. The embodiment of MTA in Example A with radiopacitizer, phosphate, and polyethercarboxylic-based superplasticizer, has high calcium oxide and leachable fluoride content, and furthermore flow-to-claylike consistency which is favorable for combined use of MTA in caries treatments such as cavity lining, base filling, temporary filling, step-wise pulp capping, etc.

The results demonstrate that there is a preferred range from 170 µl to 220 µl per gram MTA powder within which the parameters of setting time and compression strength majorly are settled, which support use of MTA powder and liquid in a capsule based mixing and dispensing system for clinical use with predictable clinical results. The results further demonstrate that the fast-setting MTA embodiment disclosed herein allows a new and wider range of treatment indications.

LIST OF REFERENCES

Biocompatibility of Dental Materials. Gottfried Schmalz, Dorthe Arenholt-Bindslev. Springer-Verlag, 2009.

Camilleri J, Montesin F E, Di Silvio L, Pitt Ford T R. The chemical constitution and biocompatibility of accelerated Portland cement for endodontic use. Int Endod J. 2005 November; 38(11):834-42.

Darvell B. W., Materials Science for Dentistry, 9th Edition. Darvell B W, 2009.

Fejerskov O, Richards A, DenBesten P (1996). The effect of fluoride on tooth mineralization. In: Fluoride in dentistry. Fejerskov O, Ekstrand J, Burt B, editors. Copenhagen: Munksgaard, pp. 112-146.

Goldberg M, Smith A J. Cells and extracellular matrices of dentin and pulp: a Biological basis for repair and tissue engineering. Crit. Rev Oral Biol Med. 2004.

Gralower R, Bielak S, Eidelman E. Observations on a calcium hydroxide lining in retrieved deciduous teeth, with proximal amalgam fillings. J Oral Rehabil. 1984 November; 11(6):561-9.

Reyes-Carmona J F, Felippe M S, Felippe W T. Biomineralization ability and interaction of mineral trioxide aggregate and white portland cement with dentin in a phosphate-containing fluid. J Endod. 2009 May; 35(5):731-6.

Schweikl H, Spagnuolo G, Schmalz G. Genetic and cellular toxicology of dental resin monomers. J Dent Res. 2006 October; 85(10):870-7. Review.

Tomson P L, Grover L M, Lumley P J, Sloan A J, Smith A J, Cooper P R. Dissolution of bio-active dentine matrix components by mineral trioxide aggregate. J Dent. 2007; 35(8): 636-42.

Wiegand A, Buchalla W, Attin T. Review on fluoride-releasing restorative materials-fluoride release and uptake characteristics, antibacterial activity and influence on caries formation. Dent Mater. 2007 March; 23(3):343-62, 2006. Review.

The invention claimed is:

1. A fluoride mineral trioxide aggregate dental material for use in caries treatment which comprises:
    a) more than 50%, a flash setting high aluminate cement powder or portland cement-like powder without gypsum addition, comprising:
        more than 60% calcium oxide (C);
        more than 15% silica (S), such that it comprise more than 50% calcium silicates including alite (tricalcium silicate or C3S) and belite (dicalcium silicate or C2S), with a C/S ratio above 2.0;
        more than 3% alumina (A), such that it comprises more than 7% calcium aluminates (CA);
        less than 10% sulphates ($SO_3$);
        altogether with a particle surface area of more than 200 $m^2$/kg; and
    b) 0.001-49.9% by dry weight of one or more fluorine-containing additives with a particle surface area of 200 to 300,000 $m^2$/kg; and
    c) 1-49.9% by dry weight of one or more further additives with a particle surface area of 200 to 300,000 $m^2$/kg; and
    d) a hydration liquid optionally comprising more than 0.001% by weight of the liquid of one or more soluble powder additives; and
    e) 0.001-10.0% by weight of the liquid of one or more superplasticizers; and
        wherein said hydration liquid, d), constitutes 10-45% by weight based on the total MTA weight of a)-e).

2. The dental material according to claim 1, wherein one or more fluoride-containing additives, b), are selected from finely particulated calcium fluoride ($CaF_2$), stannous fluoride ($SnF_2$), strontium fluoride ($SrF_2$), calcium monofluorophosphate ($Ca_2FPO_3$), sodium monofluorophosphate ($Na_2FPO_3$), sodium hexafluorosilicate ($Na_2SiF6$), fluoroapatite ($Ca_5(PO_4)_3F$), organic fluoride/amine fluoride (Org/AmF), and mixtures thereof.

3. The dental material according to claim 1, which comprises 0.1-20% by dry weight of one or more fluorine-containing additives.

4. The dental material according to claim 1, wherein the further additive, c), includes a radiopacitizer with one or more kinds of atoms having an atomic weight which is higher than the atom weight of calcium.

5. The dental material according to claim 1, wherein the superplasticizer is selected from polycarboxylic acid or derivatives, polycarboxylate acid derivatives or salts thereof, polycarboxylates such as sodium polycarboxylate, including polyacid-based compounds containing additional hydroxyl groups, polycarboxylate ethers, polyethercarboxylates, polyetherpolycarboxylates, di- or higher ester of polycarboxylic acid, acrylic acids, acrylates, acrylic acid derivatives or salts thereof, PMMA (polymethylmethacrylate), copolymers of acrylic acid and polyacrylic acids.

6. The dental material according to claim 1, wherein the hydration liquid comprises i) 0.001-10.0% by weight of the liquid of one or more superplasticizers; and ii) more than 0.001% by weight of the liquid of one or more soluble powder additives; and water.

7. A kit for the preparation of the dental material of claim 1, comprising i) a first container comprises the ingredients a)-c), and ii) a second container comprises hydration liquid d).

8. A kit for the preparation of the dental material of claim 1, comprising i) a first container comprising the ingredients a)-c) and at least a portion of the one or more superplasticizers and/or the one or more soluble powder additives, and ii) a second container comprising the remaining components of the hydration liquid d).

9. A kit for the preparation of the dental material of claim 1, comprising i) a first container comprising the ingredients a)-c), ii) a second container comprising at least a portion of the one or more superplasticizers and/or the one or more soluble powder additives, and iii) a third container comprising the remaining components of the hydration liquid d).

10. A fluoride-releasing mineral trioxide aggregate dental material which comprises:
    a) more than 50% by dry weight of a flash setting high aluminate cement powder or portland cement-like powder without gypsum addition, comprising:
        more than 60% calcium oxide (C);
        more than 15% silica (S), such that it comprise more than 50% calcium silicates including alite (tricalcium silicate or C3S) and belite (dicalcium silicate or C2S), with a C/S ratio above 2.0;

more than 3% alumina (A), such that it comprises more than 7% calcium aluminates (CA);
less than 10% sulphates ($SO_3$);
altogether with a particle surface area of more than 200 $m^2$/kg,
b) 0.001-49.9% by dry weight of one or more fluorine-containing additives with a particle surface area of 200 to 300,000 $m^2$/kg;
c) 1-49.9% by dry weight of one or more further additives with a particle surface area of 200 to 300,000 $m^2$/kg;
d) a hydration liquid optionally comprising more than 0.001% by weight of the liquid of one or more soluble powder additives; and
e) 0.001-10.0% by weight of the liquid of one or more superplasticizers; and
wherein said hydration liquid, d), constitutes 10-45% by weight based on the total MTA weight of a)-e).

11. The dental material according to claim 10, wherein one or more fluoride-containing additives, b), are selected from finely particulated calcium fluoride ($CaF_2$), stannous fluoride ($SnF_2$), strontium fluoride ($SrF_2$), calcium monofluorophosphate ($Ca_2FPO_3$), sodium monofluorophosphate ($Na_2FPO_3$), sodium hexafluorosilicate ($Na_2SiF6$), fluoroapatite ($Ca_5(PO_4)_3F$), organic fluoride/amine fluoride (Org/AmF), and mixtures thereof.

12. The dental material according to claim 10, which comprises 0.1-20% by dry weight of one or more fluorine-containing additives.

13. The dental material according to claim 10, wherein the further additive, c), includes a radiopacitizer with one or more kinds of atoms having an atomic weight which is higher than the atom weight of calcium.

14. The dental material according to claim 10, wherein the superplasticizer is selected from polycarboxylic acid or derivatives, polycarboxylate acid derivatives or salts thereof, polycarboxylates such as sodium polycarboxylate, including polyacid-based compounds containing additional hydroxyl groups, polycarboxylate ethers, polyethercarboxylates, polyetherpolycarboxylates, di- or higher ester of polycarboxylic acid, acrylic acids, acrylates, acrylic acid derivatives or salts thereof, PMMA (polymethylmethacrylate), copolymers of acrylic acid and polyacrylic acids.

15. The dental material according to claim 10, wherein the hydration liquid comprises i) 0.001-10.0% by weight of the liquid of one or more superplasticizers; and ii) more than 0.001% by weight of the liquid of one or more soluble powder additives; and water.

16. A kit for the preparation of the dental material of claim 10, comprising i) a first container comprises the ingredients a)-c), and ii) a second container comprises hydration liquid d).

17. A kit for the preparation of the dental material of claim 10, comprising i) a first container comprising the ingredients a)-c) and at least a portion of the one or more superplasticizers and/or the one or more soluble powder additives, and ii) a second container comprising the remaining components of the hydration liquid d).

18. A kit for the preparation of the dental material of claim 10, comprising i) a first container comprising the ingredients a)-c), ii) a second container comprising at least a portion of the one or more superplasticizers and/or the one or more soluble powder additives, and iii) a third container comprising the remaining components of the hydration liquid d).

* * * * *